United States Patent [19]

Burt

[11] Patent Number: 4,894,481

[45] Date of Patent: Jan. 16, 1990

[54] METHOD OF MAKING CYCLIC ARYL CHLOROPHOSPHITES

[75] Inventor: Edward A. Burt, Baton Rouge, La.

[73] Assignee: Ethyl Corporation, Richmond, Va.

[21] Appl. No.: 215,283

[22] Filed: Jul. 5, 1988

[51] Int. Cl.$^4$ ............................................. C07F 9/02
[52] U.S. Cl. .................................................... 568/12
[58] Field of Search ............................. 568/12; 556/68

[56] References Cited

U.S. PATENT DOCUMENTS

| | | | |
|---|---|---|---|
| 2,739,948 | 3/1956 | D'Alelleo | 546/350 |
| 3,281,506 | 10/1966 | Shepard et al. | 558/96 |
| 4,312,818 | 1/1982 | Maul et al. | 558/96 |
| 4,318,845 | 3/1982 | Spivac et al. | 524/91 |
| 4,322,527 | 3/1982 | Rasberger | 544/157 |
| 4,440,696 | 4/1984 | Maul et al. | 558/96 |

OTHER PUBLICATIONS

Odorisio et al., "Phosphorus and Sulfur", (1) vol. (15), pp. 9–13, 1983; (2) vol. (19), pp. 1–10, 1984; (3) vol. (19), pp. 285–293, 1984.

*Primary Examiner*—John Doll
*Assistant Examiner*—Stuart L. Hendrickson
*Attorney, Agent, or Firm*—W. G. Montgomery; J. D. Odenweller

[57] ABSTRACT

Cyclic chlorophosphites of ortho-bridged phenols are made by reaction of an ortho-bridged bisphenol with PCl$_3$ in an inert solvent using a catalytic amount of a polymeric compound having a pyridine skeletal structure and a cross-linked structure to promote the reaction.

17 Claims, No Drawings

METHOD OF MAKING CYCLIC ARYL CHLOROPHOSPHITES

BACKGROUND OF THE INVENTION

Reaction of PCl3 with aromatic hydroxy compounds is known. The reaction evolves HCl and it is also known to include a stoichiometric amount of a base such as triethylamine as an HCl acceptor. A major problem with this technique is that a large amount of hydrochloride salt is formed which must be removed.

It is also known to make triaryl phosphites by the reaction of PCl3 with an aryl hydroxide using an amine, ammonium salt or amine catalyst (Maul et al. U.S. Pat. No. 4,312,818 and U.S. Pat. No. 4,440,696). Pyridine and alpha-picoline have a low catalytic effect.

A special problem arises when the desired product is a diaryl monochlorophosphite. In this case the art teaches the use of at least a stoichiometric amount of amine as an HCl scavenger (Shepard et al. U.S. Pat. No. 3,281,506).

Preparation of cyclic ortho-bridged bisphenol chlorophosphites are also taught to require the use of at least a stoichiometric amount of amine HCl scavenger ("Phosphorus and Sulfur," 1983, Vol. 15, pp. 9-13; "Phosphorus and Sulfur," 1984, Volume 19, pp. 1-10 and pp. 285-293).

Cyclic bisphenol chlorophosphites are intermediates in the synthesis of cyclic bisphenol fluorophosphites which have been found to be very effective hydrolytically stable antioxidants in polyolefins, especially in combination with known phenolic antioxidants. One such fluorophosphite of exceptional effectiveness is 2,2'-ethylidenebis(4,6-di-tert-butylphenyl) fluorophosphite as described in L. P. J. Burton U.S. Ser. 020,023 filed Feb. 27, 1987 incorporated herein by reference. M. S. Ao and L. P. J. Burton in U.S. Ser. No. 110,181 filed Oct. 19, 1987 disclose that the reaction of an orthobridged bisphenol with PCl3 to form a cyclic monochlorophosphite can be promoted by reacting phosphorous trichloride with a 2,2'-bridged phenol in an inert solvent, preferably benzene, xylene and mesitylene in the presence of a catalytic amount of a tertamine such as pyridine or a pyridine-type compound or HCl complex thereof. While this constitutes an important contribution to the art by affording a means whereby the amount of time required to produce the cyclic monochlorophosphite product is reduced, it is necessary at the completion of the reaction to remove the promoter from the product of reaction by introducing ammonia into the reaction mixture to convert the pyridine-hydrochloride catalyst to ammonium chloride and separate it from the reaction mixture as a precipitate by filtration. At the plant-size scale, this is a difficult and expensive procedure and also creates a waste disposal problem since the precipitate contains solvent used in the process which must be removed from the filter cake before disposal. Further, pyridine is freed from the catalytic complex by the introduction of ammonia into the reaction mixture which must be separated from the reaction product by distillation and recycled for reuse. This also adds to the cost of production. Also, the pyridine-HCl complex is corrosive of the metal equipment in which the product is made and has an objectionable odor.

Thus, a need exists for an improved method for promoting the reaction of an ortho-bridged bisphenol with PCl3 to form a cyclic monochlorophosphite which avoids these problems.

SUMMARY OF THE INVENTION

It has now been discovered that the reaction of an ortho-bridged bisphenol with PCl3 to form a cyclic monochlorophosphite can be promoted by conducting the reaction in an inert solvent in the presence of a cross-linked polyvinylpyridine resin. Applicant has found that with this particular type of catalyst, the cyclic monochlorophosphite product can be conveniently and easily removed from the reaction mixture at the completion of the reaction by simple decantation and is free of contamination by the catalyst. Further, the catalyst can be reactivated and reused repeatedly in subsequent reactions.

DESCRIPTION OF THE PREFERRED EMBODIMENTS

Thus, a preferred embodiment of the invention is a process for making a cyclic chlorophosphite, said process comprising reacting phosphorus trichloride with a 2,2'-bridged bisphenol in an inert solvent and in the presence of a catalytic amount of a cross-linked polymeric vinylpyridine resin.

The process can be conducted in a number of inert solvents and can even be conducted using excess PCl3 as the solvent. Inert solvents include aliphatic hydrocarbons such as hexane, cyclohexane, heptane, isooctane and the like including mixtures thereof.

The more preferred inert solvents are the aromatic solvents which boil in the range of about 80–176° C. These include benzene, toluene, xylene and mesitylene including all isomers and all mixtures of isomers and solvents.

The most preferred solvents are toluene and xylene and mixtures thereof.

The amount of solvent should be an amount that will dissolve the reactants. A useful amount is about 50–500 parts by weight solvent per 100 parts of bisphenol.

The process is applicable to any ortho-bridged bisphenol including substituted and unsubstituted bisphenols. The bridge may be a direct bond between an ortho position on each phenolic benzene ring or it may be a bridge through a bridging group such as alkylene, alkylidene, thio, polythio, —CH2SCH2—and the like.

Examples of suitable bisphenols are 2,2'-bisphenol, 2,2'-bis (4-methyl-6-tert-butyl)phenol, 2,2'-bis(4-chloro-6-tertbutylphenol), 2,2'-bis(4-methoxy-6-isopropylphenol), 3,5-di-tert-butyl-2,2'-dihydroxy-3',5'-di-sec-pentylbiphenol, 2,2,2'-thiobis(4-methyl-6-tert-butylphenol), 2,2'-(4,6-di-tert-butylphenol), di-(3-methyl-5-tert-butyl-6-hydroxybenzyl)sulfide, 2,2'-bis[4-methyl-6(alpha-methylbenzyl)phenol], 2,2,dithiobis[4,6-di(alpha-methylbenzyl)phenol]and the like.

The more preferred bisphenols are those having the structure

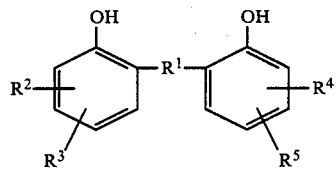

wherein $R^1$ is or is absent forming a direct bond between the benzene rings a divalent hydrocarbon bridge containing 1–6 carbon atoms and $R^2$ and $R^4$ are selected from alkyl groups containing 1–12 carbon atoms, cycloalkyl groups containing 5–8 carbon atoms and arylalkyl groups containing 6–12 carbon atoms and $R^3$ and $R^5$ are selected from hydrogen and the $R^4$ groups.

Representative examples of these preferred bisphenols are 2,2'-methylenebis(3-methyl-6-tert-butylphenol), 2,2'-methylenebis(4-methyl-6-tert-butylphenol), 2,2'-methylenebis(4-methyl6-secdodecylphenol), 2,2'-ethylidenebis(4-methyl-6-cyclopentylphenol), 2,2'-isopropylidenebis(4-6-di-cyclohexylphenol), 2,2'-butylidenebis(4-methyl-6-cyclooctylphenol), 2,2'-hexylidenebis-[6(alphamethylbenzyl)-phenol], 2,2'-methylenebis[4-methyl6(4-isopentylalphamethylbenzyl(phenol], 2,2'ethylidenebis (4-tertbutylphenol), 2,2'-bis(4,6-di-t-butylphenol), 2,2'-bis(4-methyl-6-tertbutylphenol) and the like.

In a highly preferred embodiment $R^2$, $R^3$, $R^4$ and $R^5$ are alkyls containing 1–12 carbon atoms. In a still more preferred embodiment $R^2$, $R^3$, $R^4$ and $R^5$ are located in the 4,6,4',6' positions. It is desirable that the alkyls in the 6,6' positions are tert-alkyls containing 4–12 carbon atoms. The most preferred bisphenol is 2,2,-ethylidenebis(4,6-di-tert-butylphenol).

The amount of phosphorus trichloride should be at least a stoichiometric amount. This is 1.0 mole per mole of bisphenol. Phosphorus trichloride is preferably used in excess. A preferred amount is about 1.0–20 mole of $PCl_3$ per mole of bisphenol. The large excess of $PCl_3$ can function as a solvent. A preferred amount of $PCl_3$ is about 1.0–2.0 moles per mole of bisphenol. A still more preferred amount is 1.0–1.3 moles of $PCl_3$ per mole of bisphenol.

In accordance with the present invention, the reaction is catalyzed by a vinyl polymeric resin (granular or bead-form) which has been cross-linked with divinylbenzene, divinylpyridine or other conventional crosslinking agents and which contains the pyridyl functional group covalently bonded to the vinyl polymeric backbone by the pyridyl number 2 or number 4 carbon.

The preparation of the free base, cross-linked material (poly-2- and poly-4-vinylpyridine) is described in U.S. Pat. No. 2,739,948 and follows below:

Poly-2-vinylpyridine, Cross-linked

Cross-linked copolymers of 2-vinylpyridine are made in bead form by suspension polymerization in a pressure-tight autoclave by the following procedure. To the autoclave are added (parts are given in parts by weight):

0.18 part benzoyl peroxide-dissolved in vinylpyridine
0.05 part tert-butyl perbensoate dissolved in vinylpyridine
90 parts 2-vinylpyridine
10 parts divinylbenzene (or 2,4-divinylpyridine, prepared as in U.S. Pat. No. 2,739,948)
200 parts distilled water
3 parts hydroxy apatite (sub-micronic particle size)
0.03 parts sodium oleate The autoclave is then closed and agitated by a rocking mechanism while the autoclave is immersed in a controlled-temperature bath at 90° C. for about 7 hr and then at 113°–115°C. for about 3 hr. The resultant copolymer beads are washed with dilute hydrochloric acid to remove any suspension agent, then with dilute sodium hydroxide to remove adsorbed hydrochloric acid, then with water, and subsequently dried at 70° C. for about 2 hr.

Poly-4-vinylpyridine, Cross-linked

Follow the procedure above for poly-2-vinylpyridine but substitute an equimolar quantity of 4-vinylpyridine monomer for the 2-vinylpyridine monomer.

Also, poly-4-vinylpyridine (cross-linked) may be obtained from Reillex Tar and Chemical Corp., identified as Reillex TM 402 polymer and Reillex TM 425 polymer.

Typically, the poly-2-vinylpyridine and poly-4-vinylpyridine are cross-linked with from about 2–8 percent by weight of divinylbenzene, divinylpyridine or other conventional crosslinking agents. The particle size of these polymers is not critical, but it is practical to employ the polymer resin of particle size of 0.15 to 1.7 mm.

The amount of polymer resin to be added into the reaction solution is a catalytic amount. This means that the function of the polymer is not as an HCl acceptor but is a catalytic function. Indeed, HCl will evolve from the reaction so that the polymer is not merely an HCl acceptor. The amount of polymer used is preferably much from 1.5 g to 60 g per mol of bisphenol.

The reaction is conducted at a temperature high enough to cause the reaction to proceed but not so high as to cause excessive decomposition of the reactants or products. A useful temperature range is about 50–200° C. A more preferred temperature range is about 75–150° C. Temperatures above the normal boiling point of the mixture will require a sealed reactor under pressure. It has been found that the process operates successfully without use of pressure although pressure may be used if desired. Thus, a highly preferred reaction temperature is from about 75° C. up to the reflux temperature of the reaction mixture, most preferably above about 85° C.

It has been found that the reaction rate can decrease somewhat during the course of the reaction. This is caused by the accumulation of HCl in the reaction system. This problem can be eliminated by bringing the reaction to reflux and passing a nitrogen purge through the reactor to assist in HCl removal. The nitrogen purge may be introduced as a sparge into the liquid phase or may be introduced into the vapor phase above the liquid as an inert gas sweep. Although nitrogen was used, any other inert gas could be used with equivalent results.

The reaction is readily conducted by forming a mixture of bisphenol, $PCl_3$, polymeric vinyl pyridine resin and inert solvent or a large excess of $PCl_3$ and stirring the reaction mixture at reaction temperature until the reaction is complete which usually requires about 1–6 hours. Product can be recovered by crystallizing or distilling. Optionally the reaction mixture can be used without further treatment to form the corresponding fluorophosphite as disclosed in pending application Ser. No. 110,198 filed by M. S. Ao and L. P. J. Burton.

After a period of time, the catalyst may lose some of its activity due to the build-up of solvent, reactants and reaction products on its surface. It can be easily reactivated, however by neutralizing with an alkali and reused in the reaction procedure. The reaction product which is obtained from the reaction solution is free from contamination by the catalyst and it may be concentrated under reduced pressure to a suitable volume. The concentration may be preferably carried out at a relatively low temperature such as about $-5$ ° C. to 20° C.

The manner in which the process is conducted is illustrated in the following examples.

EXAMPLE I

In a reaction vessel was placed 100 g (0.2 mol) of 2,2'-ethylidenebis(4,6-di-tert-butylphenol), 2.7 g of Reillex ™ 425 poly-4-vinylpyridine cross-linked resin and 188 g of xylene. The cross-linked vinyl polymeric resin had previously been dried in a vacuum oven at 80° C. overnight. The mixture was stirred and heated under nitrogen to 130° C. At 130° C., 37.5 g (0.3 mol) of $PCl_3$ was fed to the reaction mixture incrementally over a period of 1 hr. The reaction was essentially complete in 5 hr and 15 min. An additional 3 mL of $PCl_3$ was added to the vessel shown 3 hr and 50 min after start of reaction. Rapid HCl evolution was noted. The reaction mixture was analyzed periodically by gas chromatography (GC area percent). The following table shows the compositions excluding solvent and catalyst.

| Reaction Time (min) | Composition[1] (Area Percent) | |
|---|---|---|
| | Bisphenol[2] | Chlorophoshite[3] |
| 55 | 75 | 18 |
| 90 | 53 | 38 |
| 135 | 31 | 64 |
| 240 | 22 | 72 |
| 255 | 6 | 89 |
| 315 | 0.1 | 95 |

[1]The remaining product was a hydrogen phosphonate, 2,2'-ethylidenebis(4,6-di-tert-butylphenyl) hydrogen phosphite.
[2]2,2'-ethylidenebis(4,6-di-tert-butylphenol).
[3]2,2'-ethylidenebis(4,6-di-tert-butylphenyl) chlorophosphite.

What is claimed:

1. A process of making a cyclic chlorophosphite, said process comprising reacting phosphorus trichloride with a 2,2'-bridged bisphenol in which the bridging group is a direct bond or a group selected from alkylene, alkylidene, thio, polythio and —$CH_2SCH_2$— in an inert solvent and in the presence of a catalytic amount of a solid cross-linked polyvinylpyridine resin wherein the cross-linking agent is divinylbenzene or divinylpyridine.

2. A process of claim 1 wherein said polyvinylpyridine is cross-linked with divinylbenzene.

3. A process of claim 1 wherein said polyvinylpyridine resin is cross-linked with divinylpyridine.

4. A process of claim 1 wherein said cross-linked polyvinylpyridine resin is poly-4-vinylpyridine cross-linked with divinylbenzene.

5. A process of claim 1 wherein the particle size of the cross-linked polyvinylpyridine resin is from 0.15 to 1.7 mm.

6. A process of claim 1 wherein said inert solvent is an aromatic hydrocarbon having a normal boiling point in the range of 80–176° C.

7. A process of claim 6 wherein said solvent is xylene and said cross-linked polyvinylpyridine resin is poly-4-vinylpyridine pyridine cross-linked with divinylbenzene.

8. A process of claim 6 wherein said 2,2'-bridged bisphenol has the structure

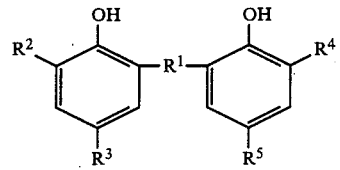

wherein R' is a divalent hydrocarbon bridge containing 1–6 carbon atoms or is absent forming a direct bond between the benzene rings and $R^2$ and $R^4$ are independently selected from alkyl groups containing 1–12 carbon atoms, cycloakyl groups containing 5–8 carbon atoms and arylalkyl groups containing 7–12 carbon atoms and $R^3$ and $R^5$ are independently selected from hydrogen and the $R^4$ groups.

9. A process of claim 8 wherein said solvent is toluene, xylene, or mixtures thereof.

10. A process of claim 9 wherein said cross-linked polyvinylpyridine resin is poly-4-vinylpyridine cross-linked with divinylbenzene.

11. A process of claim 10 wherein $R^2$, $R^3$, $R^4$ and $R^5$ are alkyl groups and are in the 4,6,4, and 6' positions respectively.

12. A process of claim 11 wherein $R^2$, $R^3$, $R^4$ and $R^5$ are tert-butyl groups.

13. A process of claim 12 wherein $R^1$ is a methylene bridge.

14. A process of claim 12 wherein $R^1$ is an ethylidene bridge.

15. A process of claim 12 wherein an inert gas purge is passed through or over the reaction mixture to assist in removing HCl.

16. A process of claim 13 wherein $R^1$ is a methylene bridge.

17. A process of claim 13 wherein $R^1$ is an ethylidene bridge.

* * * * *

UNITED STATES PATENT AND TRADEMARK OFFICE
CERTIFICATE OF CORRECTION

PATENT NO.   : 4,894,481
DATED        : JANUARY 16, 1990
INVENTOR(S)  : EDWARD A. BURT

It is certified that error appears in the above-identified patent and that said Letters Patent is hereby corrected as shown below:

Column 6, line 9 reads "vinylpyridine pyridine" and should read -- vinylpyridine -- .

Column 6, line 36 reads "4,6,4," and should read -- 4,6,4' -- .

Column 6, line 46 reads "HC1" and should read -- HCl -- .

Signed and Sealed this

Fourth Day of December, 1990

Attest:

HARRY F. MANBECK, JR.

Attesting Officer

Commissioner of Patents and Trademarks